United States Patent [19]

Moore

[11] Plant 4,366

[45] Jan. 16, 1979

[54] ROSE PLANT

[76] Inventor: Ralph S. Moore, 2519 E. Noble Ave., Visalia, Calif. 93277

[21] Appl. No.: 866,767

[22] Filed: Jan. 3, 1978

[51] Int. Cl.[2] ..... A01H 5/00

[52] U.S. Cl. ..... Plt./7

[58] Field of Search ..... Plt./7

*Primary Examiner*—Robert E. Bagwill

[57] ABSTRACT

The subject of this disclosure is a new and distinct variety of miniature rose primarily distinguished by the unique blending of yellow and pink colors, the well shaped buds and flowers, and the distinct fresh peach fruity fragrance.

1 Drawing Figure

1

The present invention relates to a new and distinct variety of hardy, dwarf, bush type rose plant of the miniature class; the variety being primarily characterized—as to novelty—by buds of typical hybrid tea form and of a color blending from yellow at base through shades of peach and pink toward the tip, and flowers which in general color effect are similar to Baby Darling (miniature — U.S. Plant Pat. No. 2,682).

The variety is further characterized by:

An abundance of bloom, with flowers usually borne several to the stem in loose cluster (sometimes singly). Fresh peach fragrance.

A plant which is vigorous, of rounded much branched shape with small semi-glossy foliage with pointed leaflets; the buds and flowers being similar in form and size to Sheri Anne (miniature — U.S. Plant Pat. No 3,826).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Little Darling (Floribunda — U.S. Plant Pat. No. 1,581, expired) as the seed parent and New Penny (miniature — not patented) as the pollen parent.

Subsequent to origination of the variety I successfully asexually reproduced it at Sequoia Nursery, located at Visalia, Calif., by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety name: AVANDEL.

Flowers borne: Singly and several together (3 to 5) on slender wirey stems.

2

Quantity of bloom: Abundant both outside and in greenhouse.

Bud: Peduncle — medium length; slender but sturdy; erect; medium green, sometimes tinted bronze (outdoors); hairs — numerous, very short (similar to peach fuzz). Before calyx breaks; size — small. Form: pointed with several foliaceous appendages and short fuzz-like hairs on surface of bud; with foliaceous parts extending beyond the tip of the bud equal to one-half or more of its length. Color — medium green, occasionally tinted with bronze (outdoors). As calyx breaks, color — yellow — near Buttercup Yellow 5/2 (sometimes greenish at base) and shading or blending into peach or orange-pink on upper ½ of petal. Opening: opens well in all weather.

Bloom: Size when fully open — small, averaging about 35–40 mm. Petalage — double — average about 25–30 petals, arranged regularly plus sometimes a few small petaloids. Form — full at first, becoming more open in the center, with petals rolled loosely outward, and later at maturity open with petals rolled loosely outward and downward. Open flowers show stamens.

Petals: Fairly thick; satiny on inside and on outside surface. Shape — outside petals, broad lanceolate, nearly round, with short acute tip; intermediate — broad lanceolate with short acute tip; inside — lanceolate with short acute tip.

Color: Newly opened flower from a plant grown in plastic greenhouse (December 1977), Visalia, Calif.

*Outside Petal.*—Outside surface — near white or soft yellow overlaid with soft pink along edge of petal. Inside surface — soft greenish yellow at base blending into soft yellow thence into soft pink (near Azalea Pink 618/2) along upper ¼ of petal.

*Intermediate Petal.*—Outside surface — similar to outside petal. Inside surface — similar to outside petal.

*Inner petal.*—Outside surface similar to intermediate petal; inside surface — similar to intermediate petal. Color on intermediate and inner petals (both surfaces) is often deeper at first than outer petals.

General color effect; newly opened flowers — blending of yellow and pink. Three days open — color similar to newly opened flowers but lighter. Behavior — opens well in all weather. Flowers tend to age to deeper pink (outdoors) a few days after opening due to action of sunlight. Spent petals drop off. Flower longevity (September 1977) — plant in pot 5 - 7 days or longer. Cut flowers at living room temperature 4 - 6 days or longer.

Reproductive Organs:

*Stamens.*—Average number, arranged regularly about pistils.

*Filaments.*—Varying length, yellow.

*Anthers.*—Well formed; yellow.

*Pollen.*—Quite abundant.

*Pistils.*—Average number.

*Styles.*—Fairly even; medium to long; bunched.

*Ovaries.*—All enclosed in calyx.

*Hips.*—Several.

*Sepals.*—Permanent; spear shaped; recurved.

*Seed.*—Several.

Foliage:

*Leaves.*—Compound of five (sometimes three or seven) leaflets; small; leathery; semi-glossy.

*Leaflets.*—Shape: broad, lanceolate; apex acute; base generally acute. Margin serrate. Color: medium green; new growth — sometimes reddish or bronze. Rachis: medium strength; upper side may have several small thorns with some tiny hairs. Stipules: medium long; narrow to medium width; medium length; long, very narrow points which turn out usually at more than 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Average to few; slender; nearly straight; inclined slightly downward; color — often reddish. Medium to short oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, much branched habit, substantially as illustrated and described, characterized by buds and flowers which are soft yellow blended with pink, resembling in color the seed parent, Little Darling (Floribunda — U.S. Plant Pat. No. 1,581, expired), and resembling the miniature rose Sheri Anne (U.S. Plant Pat. No. 2,836) in size and shape of bud and flower; and further characterized by a plant which is vigorous and compact, easy to propagate from cuttings or by budding, with an abundance of disease resistant small semi-glossy or matt foliage and an abundance of flowers having a distinct peach or nectarine fragrance, borne singly or several to the stem in loose clusters.

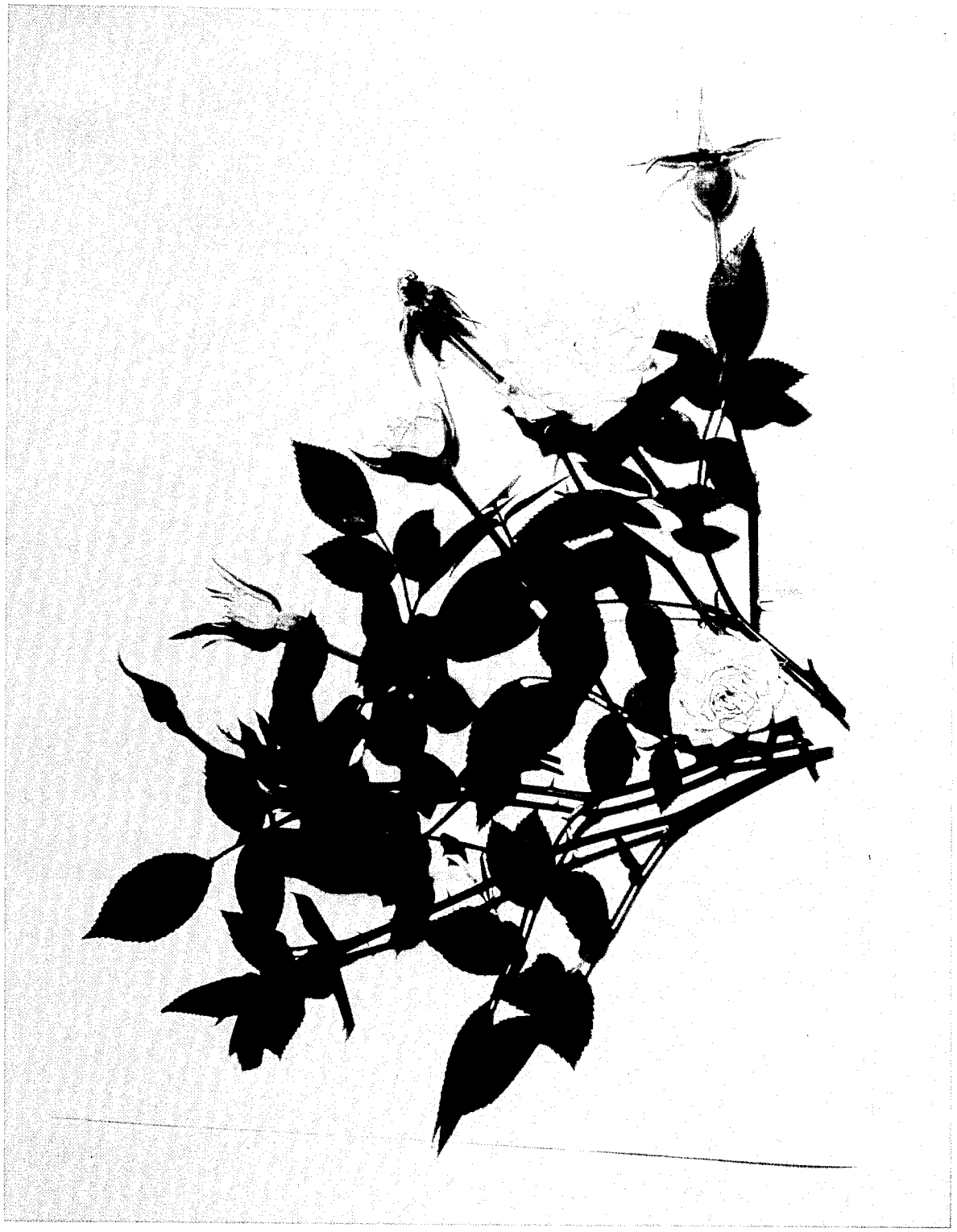

* * * * *